(12) United States Patent
Takaishi et al.

(10) Patent No.: US 9,611,280 B2
(45) Date of Patent: Apr. 4, 2017

(54) TETRAARYL BORATE COMPOUND AND METHOD FOR PRODUCING SAME

(71) Applicant: KOEI CHEMICAL COMPANY, LIMITED, Sodegaura-shi, Chiba (JP)

(72) Inventors: Satoshi Takaishi, Sodegaura (JP); Hang Jiang, Sodegaura (JP)

(73) Assignee: KOEI CHEMICAL COMPANY, LIMITED, Sodegaura-Shi (JP)

( * ) Notice: Subject to any disclaimer, the term of this patent is extended or adjusted under 35 U.S.C. 154(b) by 0 days.

(21) Appl. No.: 14/890,519

(22) PCT Filed: Apr. 24, 2014

(86) PCT No.: PCT/JP2014/002325
§ 371 (c)(1),
(2) Date: Nov. 11, 2015

(87) PCT Pub. No.: WO2014/185020
PCT Pub. Date: Nov. 20, 2014

(65) Prior Publication Data
US 2016/0108062 A1    Apr. 21, 2016

(30) Foreign Application Priority Data

May 15, 2013  (JP) ................. 2013-103340

(51) Int. Cl.
*C07F 5/02* (2006.01)
*C07C 209/68* (2006.01)
*C07C 211/08* (2006.01)

(52) U.S. Cl.
CPC .............. *C07F 5/02* (2013.01); *C07C 209/68* (2013.01)

(58) Field of Classification Search
CPC ......... C07C 209/68; C07C 211/08; C07F 5/02
USPC .......................................................... 568/6
See application file for complete search history.

(56) References Cited

U.S. PATENT DOCUMENTS 5,473,036 A * 12/1995 Piotrowski ............ C07C 211/63
528/4
5,919,983 A    7/1999 Rosen et al.
2002/0107419 A1    8/2002 Mitsui et al.
2003/0013913 A1    1/2003 Schottek et al.
2007/0197831 A1    8/2007 Lee et al.

FOREIGN PATENT DOCUMENTS

| JP | 2000507157 A | 6/2000 |
|---|---|---|
| JP | 2003518516 A | 6/2003 |
| JP | 2007530673 A | 11/2007 |
| JP | 2010-176930 * | 8/2010 |
| JP | 201148752 A | 8/2011 |
| JP | 2012025710 A | 2/2012 |
| JP | 2012149188 A | 8/2012 |
| WO | 98/40389 A1 | 9/1998 |
| WO | 2005/042147 A2 | 5/2005 |
| WO | 2005/105816 A1 | 11/2005 |
| WO | 2014/022461 A1 | 2/2014 |

OTHER PUBLICATIONS

CID 22261298 (PubChem compound record, p. 1-9, last modified Jul. 2, 2016, hereafter referred to as '298).*
SID 38396936 (Pubchem substance record, p. 1-5, available online Dec. 5, 2007, hereafter referred to as '936).*
Machine generated English language translation of JP 2012149188, obtained Jul. 8, 2016, p. 1-46.*
Machine generated English language translation of JP 2010176930, obtained Jul. 8, 2016, p. 1-11.*
Aldrich (Sigma Aldrich webpage for ammonium chloride (NH4Cl), p. 1-4, downloaded on Jul. 8, 2016).*
M. Zhou et al., "Improvement in the assessment of direct and facilitated ion transfers by electrochemically induced redox transformations of common molecular probes, table 2 to 3" Physical Chemistry Chemical Physics, 2012, 14(10), 3659-3668. (from the ISR).

* cited by examiner

*Primary Examiner* — Rosalynd Keys
*Assistant Examiner* — Amy C Bonaparte
(74) *Attorney, Agent, or Firm* — Andrews Kurth Kenyon LLP

(57) ABSTRACT

The present invention relates to a novel tetraaryl borate compound and a method for producing the same, and a method for producing a tetraaryl borate compound using the tetraaryl borate compound as an intermediate. According to the present invention, it is possible to provide a tetraaryl borate compound which has high thermal stability and can be safely handled industrially and a method for producing the same. It is also possible to provide a method for producing a tetraaryl borate compound used as a co-catalyst for a polymerization reaction using a metallocene catalyst by further reacting the tetraaryl borate compound with an amine compound.

4 Claims, No Drawings

TETRAARYL BORATE COMPOUND AND METHOD FOR PRODUCING SAME

CROSS-REFERENCE TO RELATED APPLICATIONS

This is a national phase application based on the PCT International Patent Application No. PCT/JP2014/002325 filed Apr. 24, 2014, claiming priority to Japanese Patent Application No. 2013-103340 filed May 15, 2013, the entire contents of both of which are incorporated herein by reference.

TECHNICAL FIELD

The present invention relates to a novel tetraaryl borate compound and a method for producing the same.

BACKGROUND ART

Trialkylammonium tetrakis(pentafluorophenyl) borate and (aryl)dialkylammonium tetrakis(pentafluorophenyl) borate are used as co-catalysts for a polymerization reaction using a metallocene catalyst. Examples of known methods for producing the borates include the following methods (i) and (ii) (refer to Patent Literature 1).

(i) Method for producing di(tallow-alkyl)methylammonium tetrakis(pentafluorophenyl) borate bromo magnesium tetrakis(pentafluorophenyl) borate→magnesium di[tetrakis(pentafluorophenyl) borate] magnesium di[tetrakis(pentafluorophenyl) borate]+di(tallow-alkyl)methylamine+hydrogen chloride→di(tallow-alkyl)ethylammonium tetrakis(pentafluorophenyl) borate (ii) Method for producing dimethylanilinium tetrakis(pentafluorophenyl) borate potassium tetrakis(pentafluorophenyl) borate+N,N-dimethylaniline+hydrogen chloride→dimethylanilinium tetrakis(pentafluorophenyl) borate

CITATION LIST

Patent Literature

Patent Literature 1: JP 2007-530673 W

SUMMARY OF INVENTION

Technical Problem

In the production method of (i), it is difficult to produce high purity magnesium di[tetrakis(pentafluorophenyl) borate]. As a result, it is difficult to obtain high purity di(tallow-alkyl)methylammonium tetrakis(pentafluorophenyl) borate (a purity of di(tallow-alkyl)methylammonium tetrakis(pentafluorophenyl) borate described in Patent Literature 1 is 88.6 to 89.99%). The production method of (ii) uses potassium tetrakis(pentafluorophenyl)borate, which is an alkali metal salt of tetrakis(pentafluorophenyl) borate. The alkali metal salt of tetrakis(pentafluorophenyl) borate does not have sufficient thermal stability in comparison with the tetraaryl borate compound of the present invention, represented by formula (1). Thus the alkali metal salt of tetrakis(pentafluorophenyl) borate is not suitable for industrial use in view of safe handling (see differential scanning calorimetry results of Examples described later).

Solution to Problem

The present invention has been achieved in view of the above-described problems in the related art. The present invention provides a novel tetraaryl borate compound which has high thermal stability and can be safely handled industrially, a method for producing the same, and a method for producing a tetraaryl borate compound using the tetraaryl borate compound as an intermediate.

That is, the present invention relates to a tetraaryl borate compound (hereinafter, referred to as tetraaryl borate compound (1)) represented by formula (1):

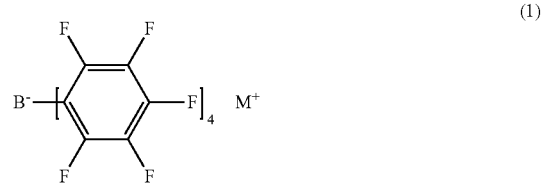

wherein $M^+$ represents $NH_4^+$;

a method for producing the tetraaryl borate compound (1), in which a magnesium halide compound (hereinafter, referred to as magnesium halide compound (2)) and an ammonium compound (hereinafter, referred to as ammonium compound (3)) are reacted, wherein the magnesium halide is represented by formula (2):

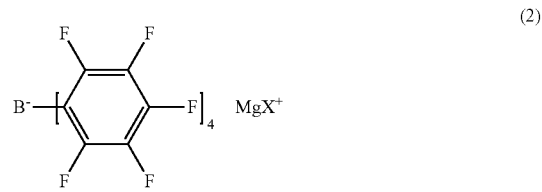

wherein X represents a halogen atom, and wherein the ammonium compound is represented by formula (3):

wherein $M^+$ is the same as above and $X^-$ represents a halogen ion; and a method for producing a tetraaryl borate compound (hereinafter, referred to as tetraaryl borate compound (5)) represented by formula (5):

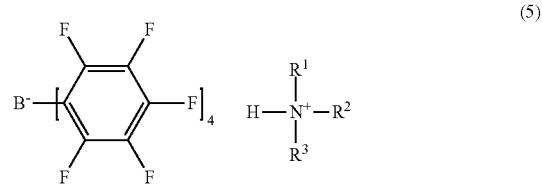

wherein $R^1$ to $R^3$ each represents an alkyl group having 1 to 30 carbon atoms or an aryl group having 6 to 30 carbon atoms, in which the tetraaryl borate compound (1) and an amine compound (hereinafter, referred to as amine compound (4)) are reacted, wherein the amine compound is represented by formula (4):

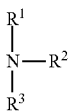

$$\begin{array}{c} R^1 \\ | \\ N-R^2 \\ | \\ R^3 \end{array} \quad (4)$$

wherein $R^1$ to $R^3$ are the same as above.

Advantageous Effects of Invention

The present invention can provide the tetraaryl borate compound (1) which has high thermal stability and is suitable for industrial use. By using the tetraaryl borate compound (1) as an intermediate, the high purity tetraaryl borate compound (5) can be produced. Therefore, the present invention is very useful industrially.

DESCRIPTION OF EMBODIMENTS

The tetraaryl borate compound (1) is produced by reacting the magnesium halide compound (2) and the ammonium compound (3) (hereinafter, this reaction is referred to as first reaction).

In formula (2), X represents a halogen atom, preferably a chlorine atom, a bromine atom, or an iodine atom, more preferably a bromine atom.

Specific examples of the magnesium halide compound (2) include chloromagnesium tetrakis(pentafluorophenyl) borate, bromomagnesium tetrakis(pentafluorophenyl) borate, and iodomagnesium tetrakis(pentafluorophenyl) borate. Preferable examples thereof include bromomagnesium tetrakis(pentafluorophenyl) borate.

In formula (3), $X^-$ represents a halogen ion, preferably a chlorine ion, a bromine ion, or an iodine ion, more preferably a chlorine ion.

Specific examples of the ammonium compound (3) include ammonium chloride, ammonium bromide, and ammonium iodide. Preferable examples thereof include ammonium chloride.

The first reaction is usually performed in a hydrocarbon solvent, an aromatic hydrocarbon solvent, an ether solvent, or a mixed solvent thereof. Among the solvents, an aromatic hydrocarbon solvent is preferably used. A use amount of a solvent is not particularly limited, but is usually 20 parts by weight or less, preferably 5 to 10 parts by weight, with respect to one part by weight of the magnesium halide compound (2).

A use amount of the ammonium compound (3) in the first reaction is usually 1 mole or more, preferably 1 to 10 moles, more preferably 2 to 5 moles, with respect to one mole of the magnesium halide compound (2).

The temperature of the first reaction is usually 10° C. or higher, preferably 20 to 50° C.

The tetraaryl borate compound (1) obtained in the first reaction is usually used for the following reaction as an aqueous solution.

The tetraaryl borate compound (1) obtained in the first reaction and the amine compound (4) are reacted to produce the tetraaryl borate compound (5) (hereinafter, this reaction is referred to as second reaction).

In formula (4), $R^1$ to $R^3$ each represents an alkyl group having 1 to 30 carbon atoms or an aryl group having 6 to 30 carbon atoms. Specific examples of the alkyl group having 1 to 30 carbon atoms include a methyl group, an ethyl group, a propyl group, a butyl group, a pentyl group, a hexyl group, a heptyl group, an octyl group, a nonyl group, a decyl group, an undecyl group, a dodecyl group, a tridecyl group, a tetradecyl group, a pentadecyl group, a hexadecyl group, a heptadecyl group, an octadecyl group, a nonadecyl group, an icosyl group, a beef-tallow-alkyl group, and a hardened-beef-tallow-alkyl group. Preferable examples thereof include a methyl group, a beef-tallow-alkyl group, and a hardened-beef-tallow-alkyl group. Specific examples of the aryl group having 6 to 30 carbon atoms include a phenyl group, a benzyl group, a phenethyl group, a methylphenyl group, and a dimethylphenyl group. Preferable examples thereof include a phenyl group.

Specific examples of the amine compound (4) include trimethylamine, triethylamine, tripropylamine, tributylamine, tripentylamine, trihexylamine, triheptylamine, trioctylamine, trinonylamine, tridecylamine, triundecylamine, tridodecylamine, tritridecylamine, tritetradecylamine, tripentadecylamine, trihexadecylamine, triheptadecylamine, trioctadecylamine, trinonadecylamine, trieicosylamine, triheneicosylamine, tridocosylamine, tritricosylamine, tritetracosylamine, tripentacosylamine, trihexacosylamine, triheptacosylamine, trioctacosylamine, trinonacosylamine, tritriacontylamine, diethylmethylamine, dipropylmethylamine, dibutylmethylamine, dipentylmethylamine, dihexylmethylamine, diheptylmethylamine, dioctylmethylamine, dinonylmethylamine, didecylmethylamine, diundecylmethylamine, didodecylmethylamine, ditridecylmethylamine, ditetradecylmethylamine, dipentadecylmethylamine, dihexadecylmethylamine, diheptadecylmethylamine, dioctadecylmethylamine, dinonadecylmethylamine, dieicosylmethylamine, diheneicosylmethylamine, didocosylmethylamine, ditricosylmethylamine, ditetracosylmethylamine, dipentacosylmethylamine, dihexacosylmethylamine, diheptacosylmethylamine, dioctacosylmethylamine, dinonacosylmethylamine, ditriacontylmethylamine, di-beef-tallow-alkylmethylamine, di-hardened-beef-tallow-alkylmethylamine, N,N-dimethylaniline, and N,N-diethylaniline. Preferable examples thereof include dihexadecylmethylamine, diheptadecylmethylamine, dioctadecylmethylamine, dinonadecylmethylamine, dieicosylmethylamine, diheneicosylmethylamine, didocosylmethylamine, ditricosylmethylamine, ditetracosylmethylamine, dipentacosylmethylamine, di-beef-tallow-alkylmethylamine, di-hardened-beef-tallow-alkylmethylamine, N,N-dimethylaniline, and N,N-diethylaniline. More preferable examples thereof include di-beef tallow-alkyl-methylamine, di-hardened-beef-tallow-alkylmethylamine, and N,N-dimethylaniline.

The second reaction is usually performed in an organic solvent. The kind of the organic solvent is not particularly limited, but is preferably a hydrocarbon solvent, an aromatic hydrocarbon solvent, an open-chain ether solvent, or a mixed solvent thereof. A use amount of the solvent is not particularly limited, but is usually 20 parts by weight or less, preferably 1 to 10 parts by weight, particularly preferably 2 to 6 parts by weight, with respect to one part by weight of the tetraaryl borate compound (1).

A use amount of the amine compound (4) in the second reaction is not particularly limited, but is usually 0.6 moles or more, preferably 0.8 to 1.5 moles, more preferably 0.9 to 1.1 moles, with respect to one mole of the tetraaryl borate compound (1).

The reaction temperature of the second reaction is usually 20° C. or higher, preferably 20 to 100° C. The reaction pressure of the second reaction is not particularly limited. The reaction may be performed under an atmospheric pressure, or if necessary, under an increased pressure or a reduced pressure. In order to remove ammonia generated as a byproduct during the reaction, the reaction is preferably performed under the atmospheric pressure or less. The reaction time of the second reaction is usually one minute or more. An upper limit of the reaction time is not particularly limited.

As a method for taking out the tetraaryl borate compound (5) as a product from a resulting reaction mixture after the second reaction is finished, for example, an organic solvent is distilled off from the reaction mixture to obtain the tetraaryl borate compound (5) as a residue. When the tetraaryl borate compound (5) as a product precipitates as a crystal in the reaction mixture, the reaction mixture is filtered to obtain the tetraaryl borate compound (5).

Specific examples of the thus obtainable tetraaryl borate compound (5) include dihexadecylmethylammonium tetrakis(pentafluorophenyl) borate, diheptadecylmethylammonium tetrakis(pentafluorophenyl) borate, dioctadecylmethylammonium tetrakis(pentafluorophenyl) borate, dinonadecylmethylammonium tetrakis(pentafluorophenyl) borate, dieicosylmethylammonium tetrakis(pentafluorophenyl) borate, diheneicosylmethylammonium tetrakis(pentafluorophenyl) borate, didocosylmethylammonium tetrakis(pentafluorophenyl) borate, ditricosylmethylammonium tetrakis(pentafluorophenyl) borate, ditetracosylmethylammonium tetrakis(pentafluorophenyl) borate, dipentacosylmethylammonium tetrakis(pentafluorophenyl) borate, di-beef-tallow-alkylmethylammonium tetrakis(pentafluorophenyl) borate, di-hardened-beef-tallow-alkylmethylammonium tetrakis(pentafluorophenyl) borate, and N,N-dimethylanilinium tetrakis(pentafluorophenyl) borate.

Hereinafter, the present invention will be described specifically based on Examples. However, the present invention is not limited in any way by these Examples. In the following Examples, $^1$H-NMR and $^{19}$F-NMR were measured at 400 MHz using a nuclear magnetic resonance apparatus AL-400 manufactured by JEOL Ltd. and using $CD_3OD$ or $CDCl_3$ as a solvent.

EXAMPLES

Example 1

Into a flask filled with nitrogen, 6.00 g (423 mmol) of boron trifluoride diethyl ether complex and 30 mL of toluene were placed. The resulting mixture was cooled in an ice bath such that the temperature was lowered to 0° C. Then, to the mixture, 140 mL (154.0 mmol) of a 1.1 mol/L pentafluorophenyl magnesium bromide solution was dropwise added over 30 minutes. Thereafter, the temperature was raised to 80° C., and the reaction was performed for 3 hours. The resulting reaction mixture was cooled in an ice bath such that the temperature was lowered to 0° C., and then water was added thereto. The mixture was separated into an organic layer and an aqueous layer to obtain the organic layer containing magnesium bromide tetrakis(pentafluorophenyl) borate. To the resulting organic layer, 60 mL of a saturated aqueous solution of ammonium chloride was added, and the resulting mixture was stirred. Thereafter, the resulting mixture was separated into an aqueous layer and an organic layer to obtain the organic layer containing ammonium tetrakis(pentafluorophenyl) borate. The resulting organic layer was concentrated under reduced pressure. Thereafter, 160 mL of methylcyclohexane and 160 mL of water were added to the residue, and the resulting mixture was stirred at 70° C. for 2 hours. The resulting mixture was separated into an organic layer and an aqueous layer to obtain 170.0 g of an aqueous solution containing ammonium tetrakis(pentafluorophenyl) borate. A $^{19}$F-NMR analysis of the obtained aqueous solution was performed. A concentration of ammonium tetrakis(pentafluorophenyl) borate in the aqueous solution was 8.6% by weight, and a yield thereof was 49.6%. A purity of ammonium tetrakis(pentafluorophenyl) borate was 99.1%.

The following is $^{19}$F-NMR analysis data of ammonium tetrakis(pentafluorophenyl) borate.

$^{19}$F-NMR($CD_3OD$) δ(ppm): −55.5 (d, 8F), −87.2 (t, 4F), −91.1 (t, 8F)

Example 2

Methylcyclohexane and 145.6 g (pure content 12.52 g, 18.0 mmol) of the 8.6% by weight ammonium tetrakis(pentafluorophenyl) borate aqueous solution obtained in Example 1 were mixed. Thereafter, 9.4 g (18.0 mmol) of ARMEEN (registered trademark) M2HT (di-hardened-beef-tallow-alkylmethylamine manufactured by Lion Akzo Co., Ltd.) was dropwise added to the resulting mixture over 10 minutes. The reaction was performed for 2 hours at 40° C. after the completion of the dropwise addition. The resulting reaction mixture was separated into an aqueous layer and an organic layer. The obtained organic layer was filtered to remove insolubles. The obtained filtrate was concentrated to obtain 21.0 g of oily di-hardened-beef-tallow-alkylmethylammonium tetrakis(pentafluorophenyl) borate (yield 97.0%). A $^{19}$F-NMR analysis of the obtained di-hardened-beef-tallow-alkylmethylammonium tetrakis(pentafluorophenyl) borate was performed. As a result, a purity thereof was 99.2%.

The following is $^1$H-NMR analysis data and $^{19}$F-NMR analysis data of di-hardened-beef-tallow-alkylmethylammonium tetrakis(pentafluorophenyl) borate.

$^1$H-NMR ($CDCl_3$) δ(ppm): 3.03 (m, 4H), 2.79 (s, 3H), 1.66 (m, 4H), 1.26 (m, 63H), 0.89 (s, 6H)

$^{19}$F-NMR ($CDCl_3$) δ(ppm): −55.2 (d, 8F), −84.7 (t, 3F), −88.9 (t, 6F)

Example 3

Sodium tetrakis(pentafluorophenyl) borate, which is an alkali metal salt of tetrakis(pentafluoro) borate, was subjected to differential scanning calorimetry using a differential scanning calorimeter (DSC-60A manufactured by Shimadzu Corporation). Further, ammonium tetrakis(pentafluorophenyl) borate of the present invention was subjected to differential scanning calorimetry in a similar manner. Measurement results thereof are shown in Table 1. As a result of the measurements, a large amount of heat generation (1.74 kJ/g) was observed at 315° C. in sodium tetrakis(pentafluorophenyl) borate. On the other hand, an exothermic peak was not observed in ammonium tetrakis(pentafluorophenyl) borate.

Conditions for differential scanning calorimetry
Sample pan: gold-plated
Rate of temperature rise: 10° C./min

TABLE 1

| | heat generation starting temperature | amount of heat generation |
|---|---|---|
| sodium tetrakis(pentafluorophenyl) borate | 315° C. | 1.74 kJ/g |
| ammonium tetrakis(pentafluorophenyl) borate | no exothermic peak | — |

Example 4

128.1 g (pure content 11.0 g, 15.8 mmol) of the 8.6% by weight ammonium tetrakis(pentafluorophenyl) borate aqueous solution obtained in Example 1 and 1.9 g of N,N-dimethylaniline (15.8 mmol) were mixed at 50° C. Thereafter, the resulting mixture was reacted at 50° C. for 5 hours. The resulting reaction mixture was a slurry. The reaction mixture was filtered at 25° C., and the resulting crystal was washed with 11 mL of water. The washed crystal was dried to obtain 122 g (yield 962%) of N,N-dimethylanilinium tetrakis(pentafluorophenyl) borate. A $^{19}$F-NMR analysis of the resulting N,N-dimethylanilinium tetrakis(pentafluorophenyl) borate was performed. As a result, a purity thereof was 100.0%.

The following is $^1$H-NMR analysis data and $^{19}$F-NMR analysis data of N,N-dimethylanilinium tetrakis(pentafluorophenyl) borate.

$^1$H-NMR(CD$_3$OD) δ(ppm): 7.41 (t, 2H), 7.22 (d, 2H), 7.15 (t, 1H), 3.12 (s, 6H)

$^{19}$F-NMR (CD$_3$OD) δ(ppm): −56.1 (s, 8F), −88.0 (t, 4F), −91.9 (s, 8F)

INDUSTRIAL APPLICABILITY

The present invention can provide the tetraaryl borate compound (1) which has high thermal stability and is suitable for industrial use. The high purity tetraaryl borate compound (5) can be produced using the tetraaryl borate compound (1) as an intermediate.

The invention claimed is:

1. A method for producing a tetraaryl borate compound of the following formula (5):

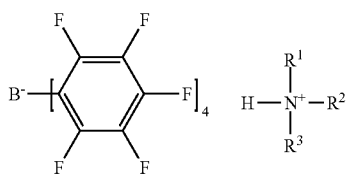

(5)

wherein R$^1$ to R$^3$ each are an alkyl group having 1 to 30 carbon atoms or an aryl group having 6 to 30 carbon atoms, wherein the tetraaryl borate compound of the following formula (1):

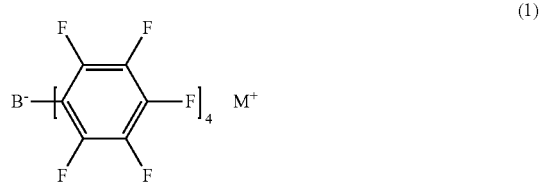

(1)

wherein M$^+$ is NH$_4^+$, and an amine compound are reacted, wherein the amine compound is of the following formula (4):

(4)

wherein R$^1$ to R$^3$ are the same as above.

2. The method for producing the tetraaryl borate compound according to claim 1, wherein R$^1$ and R$^2$ are a methyl group, an octyl group, a decyl group, a dodecyl group, a tetradecyl group, a hexadecyl group, an octadecyl group, an oleyl group, a beef-tallow-alkyl group, or a hardened-beef-tallow alkyl group.

3. The method for producing the tetraaryl borate compound according to claim 1, wherein R$^3$ is a methyl group or a phenyl group.

4. The method for producing the tetraaryl borate compound according to claim 2, wherein R$^3$ is a methyl group or a phenyl group.

* * * * *